US007442548B2

(12) United States Patent
Thomson et al.

(10) Patent No.: US 7,442,548 B2
(45) Date of Patent: *Oct. 28, 2008

(54) CULTURING HUMAN EMBRYONIC STEM CELLS IN MEDIUM CONTAINING PIPECHOLIC ACID AND GAMMA AMINO BUTYRIC ACID

(75) Inventors: James A. Thomson, Madison, WI (US); Tenneille Ludwig, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 130 days.

This patent is subject to a terminal disclaimer.

(21) Appl. No.: 11/221,516

(22) Filed: Sep. 8, 2005

(65) Prior Publication Data

US 2007/0238170 A1     Oct. 11, 2007

Related U.S. Application Data

(60) Provisional application No. 60/695,100, filed on Jun. 29, 2005, provisional application No. 60/608,040, filed on Sep. 8, 2004.

(51) Int. Cl.
*C12N 5/08* (2006.01)
*C12N 5/02* (2006.01)
(52) U.S. Cl. ........................... 435/377; 435/366
(58) Field of Classification Search .................. 435/366, 435/377, 384
See application file for complete search history.

(56) References Cited

FOREIGN PATENT DOCUMENTS

| WO | WO 03/020920 A1 | 3/2003 |
| WO | WO 2004/055155 A2 | 7/2004 |
| WO | WO 2005/068615 Z1 | 7/2005 |

OTHER PUBLICATIONS

Amit, M., et al., "Feeder Layer- and Serum-Free Culture of Human Embryonic Stem Cells," Biology of reproduction 70:837-845 (2004).
Aubert, J., et al., "Functional gene screening in embryonic stem cells implicates Wnt antogonism in neutral differentiation," Nature Biotechnology 20:1240-1245 (2002).
Carpenter, M., et al., "Properties of four human embryonic stem cell lines maintained in a feeder-free culture system," Developmental Dynamics 229:243-258 (2004).
Klimanskaya, I., et al., "Human embryonic stem cells derived without feeder cells," The Lancet 365:1636-1641 (2005).
Li, Y., et al, "Expansion of Human Embryonic Stem Cells in Defined Serum-Free Medium Devoid of Animal-Derived . . . ," Biotechnology and Bioengineering 91:688-698 (2005).
Park, H.S., et al., "Wnt activation accompanied not with maintenance of pluripotency but with differentiation of human . . . ," Anatomical Science International 79:337 (2004).
Schmidt, M., et al., "Lithium influences differentiation and tissue-specific gene expression of mouse embryonic stem (ES) cells in vitro," Int. J. Dev. Biol. 45:421-429 (2001).
Xu, Ren-He, et al., "Basic FGF and suppression of BMP signaling sustain undifferentiated proliferation of human ES cells," Nature Methods 2:185-190 (2005).
BD Matrigel Basement Membrane Matrix and BD Matrigel Basement Membrane matrix High Concentration (HC), BD Biosciences Online XP-002369813.
Evans, M.J., et al., "Establishment in culture of pluripotential cells from mouse embryos," Nature 292:154-156 (1981).
Solter, D., et al., "Immunosurgery of mouse blastocyst," Proc. Nat. Acad. Sci. USA 72:5099-5102 (1975).

*Primary Examiner*—Deborah Crouch
(74) *Attorney, Agent, or Firm*—Quarles & Brady LLP

(57) ABSTRACT

Previous methods for culturing human embryonic stem cells have required either fibroblast feeder cells or a medium which has been exposed to fibroblast feeder cells in order to maintain the stem cells in an undifferentiated state. It has now been found that if high levels of fibroblast growth factor are used in a medium with gamma amino butyric acid, pipecholic acid, lithium and lipids, the stem cells will remain undifferentiated indefinitely through multiple passages, even without feeder cells or conditioned medium. A humanized matrix of human proteins can be used as a basement matrix to culture the cells. New lines of human embryonic stem cells made using these culture conditions, the medium and the matrix, will never have been exposed to animal cells, animal products, feeder cells or conditioned medium.

9 Claims, 2 Drawing Sheets

CULTURING HUMAN EMBRYONIC STEM CELLS IN MEDIUM CONTAINING PIPECHOLIC ACID AND GAMMA AMINO BUTYRIC ACID

CROSS-REFERENCE TO RELATED APPLICATIONS

This application claims priority from U.S. provisional patent application Ser. No. 60/695,100 filed Jun. 29, 2005 and from U.S. provisional patent application Ser. No. 60/608,040 filed Sep. 8, 2004.

STATEMENT REGARDING FEDERALLY SPONSORED RESEARCH OR DEVELOPMENT

Some of the work described in this specification was supported by grants from the U.S. Government and some was not. None of the work described in this specification on the process of deriving new human embryonic stem cell lines was supported by any grant money from the U.S. Government. To that extent, this invention was made with United States government support awarded by the following agencies: NIH RR017721. The United States has certain rights in this invention.

BACKGROUND OF THE INVENTION

Stem cells are defined as cells that are capable of differentiation into many other differentiated cell types. Embryonic stem cells are stem cells from embryos which are capable of differentiation into most, if not all, of the differentiated cell types of a mature body. Stem cells are referred to as pluripotent, which describes this capability of differentiating into many cell types. A category of pluripotent stem cell of high interest to the research community is the human embryonic stem cell, abbreviated here as human ES cell, which is an embryonic stem cell derived from a human embryonic source. Human embryonic stem cells are of great scientific interest because they are capable of indefinite proliferation in culture and are thus capable, at least in principle, of supplying cells and tissues for replacement of failing or defective human tissue. The existence in culture of human embryonic stem cells offers the potential of unlimited amounts of human cells and tissues for use in a variety of therapeutic protocols and research programs to assist in human health. It is envisioned in the future human embryonic stem cells will be proliferated and directed to differentiate into specific lineages so as to develop differentiated cells or tissues which can be transplanted into human bodies for therapeutic purposes.

The basic techniques to create and culture human embryonic stem cells have been described. The previously reported techniques do work, but there are limitations and drawbacks to many of the procedures currently used to culture human embryonic stem cells. One limitation is of particular concern. Most existing human embryonic stem cell lines have been, to one degree or another, exposed directly to mouse cells or to a medium in which mouse cells have been cultured previously. The fact that some human ES cells from existing cell lines were found to exhibit the sialic residue Neu5Gc, which is not normally made by human cells, received much attention in the press. The original techniques for the generation and culture of human embryonic stem cells required the use of mouse embryonic fibroblast (MEF) feeder cells as a feeder layer on which human embryonic stem cells could be cultured. The fibroblast feeder cells acts, through some as yet incompletely understood mechanism, to encourage the stem cells to remain in an undifferentiated state. Later, it was discovered that the same phenomenon could be achieved if the stem cells were exposed to "conditioned media." Conditioned medium is nothing more than stem cell culture medium on which feeder cells, such as MEFs, had been previously been cultured. Either the feeder cells imparted some factor to the medium or removed some factor from the medium, but the result is that conditioned medium can be used to culture stem cells without differentiation. Either culture condition, the direct growth of human ES on murine feeder cells, or the use of conditioned media, raises the concern that one or more agents such as a virus could transmit from the mouse cells to the human ES cells. If one of the objectives of human embryonic stem cell cultures is to create tissues which can ultimately be transplanted into a human body, it is highly desirable that the stem cells never have been exposed to cells of another species or to media which have been used to culture cells of another species. Accordingly, defining a culture condition, which will permit the proliferation and culture of human embryonic stem cells without a fibroblast feeder layer, is of great interest in the continued development of techniques for the long term culture of human embryonic stem cells.

Several medium formulations will permit human ES cells to remain undifferentiated for some time, but that state often fails to maintain itself. In particular, we define the growth of human ES cells from an initial seed culture in a culture vessel to confluence in the same culture vessel as a "passage." We have found several medium formulations that permit the cultivation of human ES cells for one or two passages without severe differentiation, but then the cells differentiate rapidly upon subsequent passages. We have come to believe that in order for a medium to truly support the indefinite proliferation of human ES cells without differentiation, without conditioned medium or fibroblast feeder cells, the medium must be demonstrated to support culture of human ES cells in a substantially uniform and undifferentiated state for at least five passages. It is also important that the cultures remain relatively homogenous and undifferentiated throughout the culture period and retain all of the important characteristics of human ES cells.

A characteristic trait of human embryonic stem cells in culture is that if conditions are less than ideal, the cells have a tendency to differentiate. It is easy to induce human ES cells to differentiate while it is demanding to maintain the human ES cells in undifferentiated state in culture. Most culture conditions will results in some level of unwanted differentiation, particularly around the periphery of the growing ES cell colony. While ES cells can be cultured with some degree of unwanted differentiation, the objective is to define a culture condition that permits the culture to remain as undifferentiated as possible, i.e. with as few differentiated cells as possible. We believe that we have used particularly stringent standards to define conditions that will support the indefinite culture of undifferentiated ES cell cultures.

The state of differentiation of a stem cell culture can be assessed by morphological characteristics. Undifferentiated stem cells have a characteristic morphology, i.e. small and compact cells with clearly defined cell borders, a morphology which can be easily seen by examination of a stem cell culture under a microscope. By contrast, cells which have differentiated appear larger and more diffuse with indistinct borders. While some differentiated cells can, and normally do, appear at the margin of colonies of undifferentiated cells, the optimal stem cell culture is one that proliferates in the culture vessel with only minimal numbers of cells at the periphery of the culture appearing to be differentiated. With experience, one can judge the status of differentiation and health of human ES cell cultures visually with good accuracy.

In addition, the sufficiency of a medium to support the derivation of new lines of human ES cells is an even more stringent criteria for the sufficiency of stem cell culture conditions. Some culture conditions which support the expansion and growth of existing stem cells lines have not proven sufficient for use in the derivation of new human ES cell lines. It appears that the capacity to support the initiation of new lines of stem cells is a capacity that not all stem cell culture conditions will feature.

BRIEF SUMMARY OF THE INVENTION

The present invention is summarized as a method for culturing human embryonic stem cells without the need for feeder cells or conditioned medium, the method including the step of culturing the human embryonic stem cells in a medium including salts, vitamins, amino acids, glucose, a fibroblast growth factor, gamma amino butyric acid, pipecholic acid, a lithium salt and lipids, all in sufficient amount to maintain the stem cells in an undifferentiated state through multiple culture passages.

The present invention is also directed to an in vitro cell culture of human embryonic stem cells cultured in a medium including high levels of a fibroblast growth factor, gamma amino butyric acid, pipecholic acid, a lithium salt and lipids so that the stem cells can be cultured indefinitely in an undifferentiated state without the need for fibroblast feeder cells or conditioned medium.

The present invention is also summarized in the creation of new lines of human embryonic stem cells which have not been exposed to animal products, feeder cells, or conditioned medium.

It is an object of the present invention to define long term culture conditions for human embryonic stem cells that avoid the use of animal cells, whether feeder cells or for conditioning medium in which stem cells are cultured.

It is another object of the present invention to define culture conditions for human embryonic stem cells that are as defined as possible while avoiding exposure to animal cells or animal proteins.

Other objects, features and advantages of the present invention will become apparent from the following specification.

DETAILED DESCRIPTION OF THE INVENTION

Figure 1:
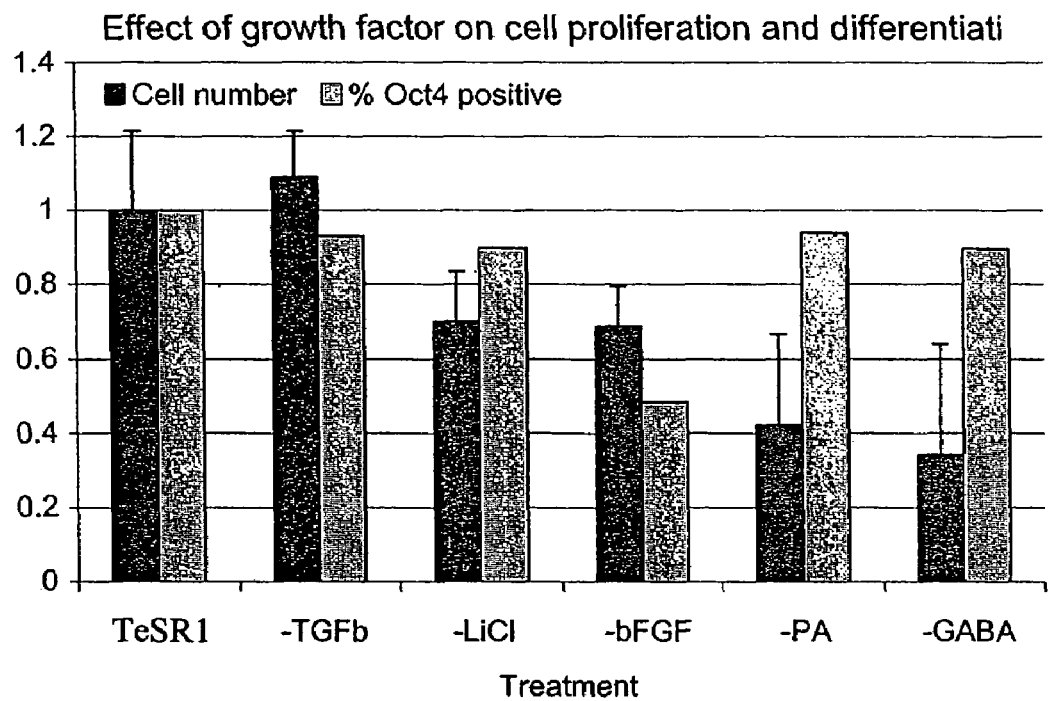
FIG. 1 is a graphical illustration of some of the data from the examples below.

We have identified multiple culture conditions and media which permit the indefinite culture and proliferation of human embryonic stem cells in an undifferentiated state and also in the complete absence of both feeder cells and conditioned medium. The culture conditions and media described here are entirely free of animal products and all proteins are of human origin. The development of these media and culture conditions make possible the derivation and maintenance of human ES cell lines in defined and controlled conditions without direct or indirect exposure to animal cells of any kind, and also makes possible the derivation of new lines of human ES cells which have never been exposed to animal cells or medium in which animal cells were cultured. The medium is free of animal products or proteins. This medium has been demonstrated to support undifferentiated ES cell proliferation through at least twenty-five passages, which is firm evidence that it will support such cultures indefinitely. The preferred medium has also now proven sufficient to support the derivation of new lines of human ES cells, and these new lines have passed through more than ten passages in culture.

It has sometime been the practice in the past to refer to the use of conditioned medium as creating "feeder-free" culture conditions. This phrase is a misnomer, since feeder cells of some type are still needed to condition the "conditioned medium." Here, culture conditions are described which permit the "feeder-independent" culture of human ES cells. By "feeder independent" it is meant that no feeder cells of any kind, human or animal, are needed anywhere in the process and are neither required for culture nor to condition the medium. Feeder independent conditions do not require feeder cells at all for any purpose.

A defined and humanized medium for the culture and proliferation of human ES cells typically includes salts, vitamins, an energy source such as glucose, minerals and amino acids. To supplement the medium and supply conditions to support cell growth, initially stem cell media included serum from one source or another. Also previously it has been reported that the addition of fibroblast growth factor plus a serum replacement additive will permit the cultivation of human ES cells without serum. The serum replacement can be a commercially available product sold for that purpose or can be a formulated mixture of protein, such as serum albumin, vitamins, minerals, a transferrin or a transferrin substitute, and insulin or an insulin substitute. This serum replacement component may also be supplemented with selenium and with a mixture of lipids. It is preferred here that a defined serum replacement additive mix be used in lieu of serum from any source in culturing human ES cells, in order to avoid the issues of variation in serum constituents and to use media that are as defined as possible. Other growth factors which have been found to be advantageous to add to the culture medium are GABA, pipecholic acid, lithium chloride, and transforming growth factor beta (TGFβ), although the TGFβ may not be needed with increasing levels of FGF added to the medium.

To avoid the need for a fibroblast feeder layer, previously thought to be necessary to maintain human ES cells in an undifferentiated state, it is reported here that the combination of the use of higher concentrations of FGF (10 to 1000 ng/ml) together with the use of gamma-aminobutyric acid (GABA), pipecholic acid, lithium chloride and TGF-beta, will enable a medium to support undifferentiated stem cell growth. The combination of these additives has been found to be sufficient to maintain the culture of human ES cells in an undifferentiated state indefinitely without exposure to either feeder cells or conditioned media. These additives are demonstrably sufficient. However, all of them may not be necessary for every medium formulation. By selective deletion of these additives, it may be empirically determined if one or more of them are not required to achieve this result for a given medium. However, it is clear that the combination is sufficient to enable a variety of media that will support the long term culture and proliferation of undifferentiated human ES cells without feeder cells or conditioned medium.

These constituents are subject to some variation. For example, the LiCl is used in the medium because it stimulates the wnt pathway. Wnts themselves or other stimulators of this pathway such as activin could be substituted as equivalents to LiCl, even though LiCl is the likely the most economical agent for this purpose. Similarly, the GABA is believed to interact with the GABA receptor, and the scientific literature includes the identification of several molecules which are agonists of that same receptor and might be substituted for GABA in the medium as an equivalent. It is also believed that PA also interacts with the GABA receptor. While both PA and GABA were found to be helpful in the medium at the concentrations used here, it is also envisioned that one or the other of these constituents could be dramatically increased in concentration to obviate the need for the other.

The fibroblast growth factor in higher concentrations (40 to 100 ng/ml) seems to obviated the need for feeder cells. The preferred FGF is basic FGF, also referred to as bFGF and FGF2, but other FGFs including at least FGF4, FGF9, FGF17 and FGF18 will suffice for this purpose as well. Other FGFs may also work, even if at higher concentrations.

It is also helpful to include in the culture conditions for the human ES cells a biological matrix in the culture vessel. One such material that has been used previously is Matrigel™, which is an artificial basement membrane of mouse cell origin, which is supplied as a commercial product free of mouse cells. However, the use of Matrigel introduces into the culture a material which is both poorly defined and which includes material of murine origin. Here it is also described how to create a biological matrix of human proteins that substitutes completely for the Matrigel. This matrix is composed of four human proteins: collagen isolated from human placenta, fibronectin isolated from human plasma, vitronectin isolated from human plasma and laminin isolated from human placenta. The combination of these four proteins is sufficient, but the use of all four may not be necessary to support the growth and culture of human ES cells. The use of such a matrix without one of vitronectin, fibronectin or laminin, but including the other three proteins, does support the culture of ES cells, with some loss in purity in the state of differentiation of the ES cells culture. The method of making the matrix for ES cell growth is described in the examples below.

Arriving at the above listed medium additives followed the methodical testing of over 80 individual growth factors. While some of the additives seemed, at least for a few passages, to support in the growth of human ES cells in culture, many failed in subsequent passages to maintain the ES cells in an undifferentiated state. We were able to identify combinations of these other factors which gave the results of the media additives described in the examples below.

The observation that human embryonic stem (ES) cell cultures have previously been maintained in an undifferentiated state only when cultured in the presence of fibroblast feeder cells or in conditioned medium has led to speculation that the fibroblasts release into the medium a factor which acts to inhibit differentiation of the ES cells. The data presented below demonstrates that this not the case. However, whatever effect that is mediated by the fibroblast feeder cells to the medium, it is now clear that the media described below will substitute for that effect. The medium described below is defined, contains no animal cells, and permits the long term culture of undifferentiated human ES cells. An example is presented of a medium in which the proteins in the medium are all human, to have a "humanized" medium and matrix to avoid any possible concerns about sub-cellular products of animal origin.

Also described below is the derivation of new lines of human embryonic stem cells using this medium. These lines of human ES cells have thus never been exposed to feeder cells, conditioned medium, animal products or animal proteins. It has previously been reported that prior human ES lines exhibit a sialic acid form (Neu5Gc) that is not natively found in human cells whether in culture or in the body. Since the prior human ES lines acquired the Neu5Gc from culture conditions including murine components, the new human ES cell lines described here will be and are entirely free of Neu5Gc.

EXAMPLES

The constituents of TeSR1 medium, which was used for all cultures described here unless otherwise indicated, is set forth in Table 1 below. Our preliminary experiments suggested that undifferentiated human ES cell proliferation was optimal at a pH of 7.2, an osmolarity of 350 mOsMol, and an atmosphere of 10% $CO_2$/5%$O_2$. These conditions were used for all subsequent cultures described here.

While a medium with all of the above constituents is sufficient and is preferred, not all of the components are necessary for the successful culture of human ES cells. Depending on the amount of differentiated cells one is willing to tolerate, some the components of the medium can be omitted in a medium, particularly if the medium is only used for a few passages. To explore which constituents might be omitted, human ES cells were cultured on variants of the above medium with differing components omitted. Two hundred thousand cells were plated and grown for 7 days on the experimental media, two wells per treatment. The cells were then assayed for expression of the transcription factor Oct4, a recognized marker of undifferentiated cells. The data from that experiment is presented as a graph in FIG. 1, where the numbers of Oct4 expressing cells in each experimental medium are presented as a fraction of that from the preferred medium TeSR1. Note that TGFβ seems to be the least necessary component, at least in the presence of high levels of FGF for short term culture. Note also that other constituents omitted do result in increased percentages of undifferentiated cells, but the differences are quantitative, and the medium does work, at least to some degree for limited cell passages, without those components.

The medium has also been used to culture human ES cells using a new matrix material of human origin. The new matrix is composed of the following four proteins:

1. Collagen (isolated from human placenta) at a final concentration of 10 μg/100 μl/$cm^2$.
2. Fibronectin (isolated from human plasma) at a final concentration of 5 μg/100 μl/$cm^2$.
3. Vitronectin (isolated from human plasma) at a final concentration of 0.2 μg/100 μl/$cm^2$.
4. Laminin (isolated from human placenta) at a final concentration of 5 μg/100 μl/$cm^2$.

To assemble this matrix, the collagen is denatured with 6M GuHCl (guanidine HCl), filtered through a 0.45 micron filter and frozen in aliquots. Upon thaw, denatured collagen was diluted into a Ca and Mg free PBS to achieve the appropriate final concentration and plated. The coated plates were allowed to incubate at room temperature for no less than 1 hour before the additional matrix components were plated. Following this initial incubation, additional matrix components (Fibronectin, Vitronectin and Laminin) were diluted into a Ca and Mg free PBS to achieve the appropriate final concentration and plated. The coated plates were allowed to incubate at room temperature for no less than 1 hour before human ES cells were plated.

Using the new matrix material, human ES cells of previously existing lines have been cultured for a minimum of 10 passages while remaining undifferentiated and proliferating.

Figure 2:
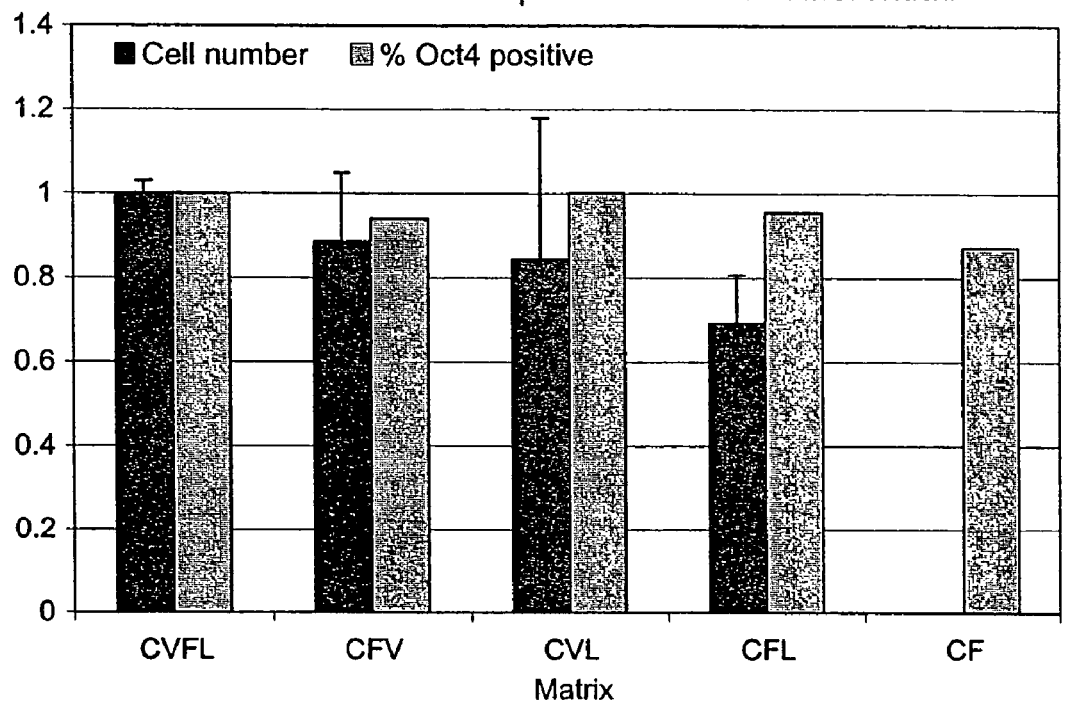
FIG. 2 is an additional graphical illustration of data from the examples below.

To test the strict necessity for the components of the humanized matrix, variations on the matrix were formulated with one or more components omitted. The data from that experiment is presented in FIG. 2. The letter initials for each experimental condition represent the proteins in the matrix (C-collagen, F-fibronectin, V-vitronectin, and L-laminin). Note that CFV, CVL and CFL membranes do work well and maintain ES cells in an undifferentiated state, but are simply not quite as conducive to cell culture growth as the CVFL matrix condition.

This medium has also proven capable of supporting the initiation of new lines of human embryonic stem cells. The derivation process for new lines can be a difficult test for medium formulations, but the use of the defined medium makes it possible to create new lines of human embryonic stem cells which have not been exposed to animal proteins or matices, and never been exposed to feeder cells or medium in which feeder cells were cultured. This is believed to be a novel achievement.

This work was undertaken only after obtaining institutional review board approval and informed consent from the donors. Frozen human embryos which were created for human in vitro fertilization protocols, but were in excess of clinical needs, were donated. The embryos were thawed and cultured to the blastocyst stage using a commercially available sequential embryo culture system (Vitrolife-GIII series). After removal of the zona pellucida, the inner cell mass (ICM) of the human blastocysts were isolated either by immunosurgery (Solter and Knowles, 1975, *Proc. Natl. Acad. Sci. USA*, 72:5099-5102) or as cultured whole mounts (Evans and Kaufman, 1981, *Nature*, 292154-156) and plated in 4-well culture plates onto the defined medium TeSR1 with the defined humanized matrix as described above (CVFL). Following an initial 48 hours of culture, the TeSR1 culture medium was replaced on a daily basis. After 14 to 21 days, clumps of cells were mechanically isolated and replated onto fresh CVFL plates. Mechanical isolation was continued for the subsequent 2 to 3 passages after which the colonies were passaged using the enzyme dispase. The new colonies were confirmed to be new lines of human embryonic stem cells.

Using TeSR1 medium on the four human matrix components identified above, we have derived two new human ES cell lines from 5 cultured blastocysts. As of this writing, both human ES cell lines have now been continuously in culture for 6 months through successive passaging. The lines are stable and morphologically similar to previous stem cell lines. FACS analysis and RT-PCR, and Western blotting demonstrated that these cells express a series of markers characteristic of human ES cells. Embryoid bodies derived from these cell lines expressed markers of all three germ layers, and both cell lines formed teratomas when injected into SCID-beige mice. After 4 months in culture, one cell line was XXY (Klinefelter Syndrome) and the other was karyotypically normal. Klinefelter Syndrome is one of the most common human chromosome abnormalities, suggesting that this abnormality may have been present in the embryo itself rather than an artifact introduced by the process of initiating the stem cell culture.

TABLE 1

| Complete Formulation for TeSR1 Medium | |
|---|---|
| | mM |
| INORGANIC SALTS | |
| Calcium chloride (Anhydrous) | 0.8232 |
| HEPES | 11.76 |
| Magnesium chloride (Anhydrous) | 0.2352 |
| Magnesium Sulfate (MgSO4) | 0.319088 |
| Potassium chloride (KCl) | 3.26144 |
| Sodium bicarbonate (NaHCO3) | 11.2112 |
| Sodium chloride (NaCl) | 94.55824 |
| Sodium phosphate, dibasic (Anhydrous) | 0.392 |
| Sodium phosphate, mono. (NaH2PO4-H20) | 0.355152 |
| TRACE MINERALS | |
| Ferric Nitrate (Fe(NO3)3-9H2O) | 0.00009408 |
| Ferric sulfate (FeSO4-7H2O) | 0.001176 |
| Cupric sulfate (CuSO4-5H2O) | 4.0768E−06 |
| Zinc sulfate (ZnSO4-7H2O) | 0.001176 |
| Ammonium Metavanadate NH4VO3 | 0.000056 |
| Mangenous Sulfate Mn SO4 H2O | 1.00592E−05 |
| Ammonium Molybdate | 1.00404E−05 |
| NiSO4 6H2O | 4.94861E−06 |
| Sodium Meta Silicate Na2SiO3 9H2O | 0.004926108 |
| SnCl2 | 5.32544E−06 |
| CdCl2 | 6.21931E−05 |
| CrCl3 | 9.41176E−06 |
| AgNo3 | 5.00293E−06 |
| AlCl3 6H2O | 2.4855E−05 |
| Ba (C2H3O2)2 | 4.99217E−05 |
| CoCl2 6H2O | 5.0021E−05 |
| GeO2 | 2.5337E−05 |
| KBr | 5.04202E−06 |
| KI | 5.12048E−06 |
| NaF | 0.000500119 |
| RbCl | 5.00414E−05 |
| ZrOCl2 8H20 | 9.03834E−05 |
| GROWTH FACTORS | |
| GABA | 0.979 |
| Pipecholic Acid | 0.000984 |
| bFGF | 5.80E−06 |
| LiCl | 0.979 |
| TGF beta 1 | 2.35E−08 |
| LIPIDS | |
| Linoleic Acid | 0.0070976 |
| Lipoic Acid | 0.00039984 |
| Arachidonic Acid | 0.001312 |
| Cholesterol | 0.0113798 |
| DL-alpha tocopherol-acetate | 0.02962 |
| Linolenic Acid | 0.007184 |
| Myristic Acid | 0.008758 |
| Oleic Acid | 0.00708 |
| Palmitoleic Acid | 0.007862 |
| Stearic Acid | 0.00703 |
| AMINO ACIDS | |
| L-Alanine | 0.1392 |
| L-Arginine hydrochloride | 0.5488 |
| L-Asparagine-H2O | 0.1392 |
| L-Aspartic acid | 0.1392 |
| L-Cysteine-HCl—H2O | 0.0784 |
| L-Cystine 2HCl | 0.0784 |
| L-Glutamic acid | 0.1392 |
| L-Glutamine | 2.96 |
| Glycine | 0.296 |
| L-Histidine-HCl—H2O | 0.1176 |
| L-Isoleucine | 0.326144 |
| L-Leucine | 0.353584 |
| L-Lysine hydrochloride | 0.391216 |
| L-Methionine | 0.090944 |
| L-Phenylalanine | 0.16856 |
| L-Proline | 0.2176 |
| L-Serine | 0.296 |
| L-Threonine | 0.352016 |
| L-Tryptophan | 0.0346528 |
| L-Tyrosine 2Na 2H2O | 0.167776 |
| L-Valine | 0.354368 |

TABLE 1-continued

Complete Formulation for TeSR1 Medium

| | mM |
|---|---|
| VITAMINS | |
| Ascorbic acid | 0.375 |
| Biotin | 1.12112E−05 |
| Choline chloride | 0.0502544 |
| D-Calcium pantothenate | 0.0036064 |
| Folic acid | 0.004704 |
| i-Inositol | 0.05488 |
| Niacinamide | 0.012936 |
| Pyridoxine hydrochloride | 0.0076048 |
| Riboflavin | 0.0004704 |
| Thiamine hydrochloride | 0.02460217 |
| Vitamin B12 | 0.000392 |
| ENERGY SUBSTRATES | |
| D-Glucose | 13.72784 |
| Sodium Pyruvate | 0.392 |
| PROTEINS | |
| Human Insulin | 0.0034438 |
| Human Holo-Transferrin | 0.14 |
| Human Serum Albumin | 199.7 |
| OTHER COMPONENTS | |
| Glutathione (reduced) | 0.00592996 |
| Hypoxanthine Na | 0.01176 |
| Phenol red | 0.0159936 |
| Putrescine-2HCl | 0.000394352 |
| Thymidine | 0.001176 |
| 2-mercaptoethanol | 0.1 |
| Selenium | 0.000177304 |
| Pluronic F-68 | 0.238 |
| Tween 80 | 0.3358 |

We claim:

1. A method for initiating a new cultured line of human embryonic stem cells without the use of feeder cells or conditioned medium, the method comprising the step of
plating cells from a blastocyst onto a matrix in a medium including albumin, minerals, vitamins, amino acids, glucose, a fibroblast growth factor, gamma amino butyric acid, pipecholic acid, lithium, lipids, a transferrin or a transferrin substitute and insulin or an insulin substitute in sufficient amounts to originate and maintain a new proliferating stem cell line in an undifferentiated state.

2. The method of claim 1 wherein the medium includes the fibroblast growth factor in a concentration of at least 40 ng/ml.

3. An in vitro cell culture comprising in a culture vessel:
human embryonic stem cells;
a culture medium, the culture medium comprising albumin, minerals, salts, vitamins, amino acids, glucose, a fibroblast growth factor, gamma amino butyric acid, pipecholic acid, lithium, lipids, a transferrin or a transferrin substitute and insulin or an insulin substitute in sufficient amounts to maintain the stem cells in an undifferentiated state through multiple culture passages, the medium being free of feeder cells and never having been exposed to feeder cells; and
a humanized matrix made from human collagen and at least two of human proteins selected from fibronectin, vitronectin and laminin.

4. The culture of claim 3 wherein the matrix includes all of collagen, fibronectin, vitronectin and laminin.

5. The culture of claim 3 wherein the medium includes the fibroblast growth factor in a concentration of at least 40 ng/ml.

6. An in vitro cell culture comprising in a culture vessel:
human embryonic stem cells;
a humanized matrix made from human collagen and at least two of the human proteins selected from fibronectin, vitronectin and laminin; and
a culture medium, the culture medium comprising albumin, minerals, vitamins, amino acids, glucose, a fibroblast growth factor, lipids, a transferrin or a transferrin substitute, insulin or an insulin substitute, and at least two members selected from gamma amino butyric acid, pipecholic acid, and lithium in sufficient amounts to maintain the stem cells in an undifferentiated state through multiple culture passages, the medium being free of feeder cells and never having been exposed to feeder cells.

7. A method of culturing new human embryonic stem cells comprising the steps of
(a) isolating the inner cell mass of an embryo in the blastocyst stage;
(b) culturing the cells from step (a) in a medium including albumin, minerals, vitamins, amino acids, glucose, a fibroblast growth factor, gamma amino butyric acid, pipecholic acid, lithium, lipids, a transferrin or a transferrin substitute and insulin or an insulin substitute in sufficient amounts to maintain the stem cells in an undifferentiated state through multiple culture passages, the culturing step being conducted on a matrix of human proteins comprising at least three of the proteins selected from collagen, fibronectin, vitronectin, and laminin; and
(c) serially expanding the new cells which proliferate on the medium.

8. A culture of cells comprising human embryonic stem cells growing on a matrix of human proteins that comprises at least three of the proteins selected from collagen, fibronectin, vitronectin, and laminin, the stem cells from a lineage which has never been exposed to animal cells, animal proteins, feeder cells or conditioned medium, the cell culture medium comprising albumin, minerals, vitamins, amino acids, glucose, a fibroblast growth factor, gamma amino butyric acid, pipecholic acid, lithium, lipids, a transferrin or a transferrin substitute, and insulin or an insulin substitute capable of maintaining the cells through over twenty passages in culture while the cells remain undifferentiated, maintain pluripotency and maintain normal karyotype.

9. A culture of cells comprising human embryonic stem cells which do not exhibit the sialic acid Neu5Gc, wherein the culture comprises (i) human embryonic stem cells on a matrix of human proteins that comprises at least three of collagen, fibronectin, vitronectin, or lamiin and (ii) a cell culture medium that comprises albumin, minerals, vitamins, amino acids, glucose, a fibroblast growth factor, lipids, a transferrin or a transferrin substitute, insulin or an insulin substitute, and at least two members selected from gamma amino butyric acid, pipecholic acid, and lithium.

* * * * *